Figure 2:
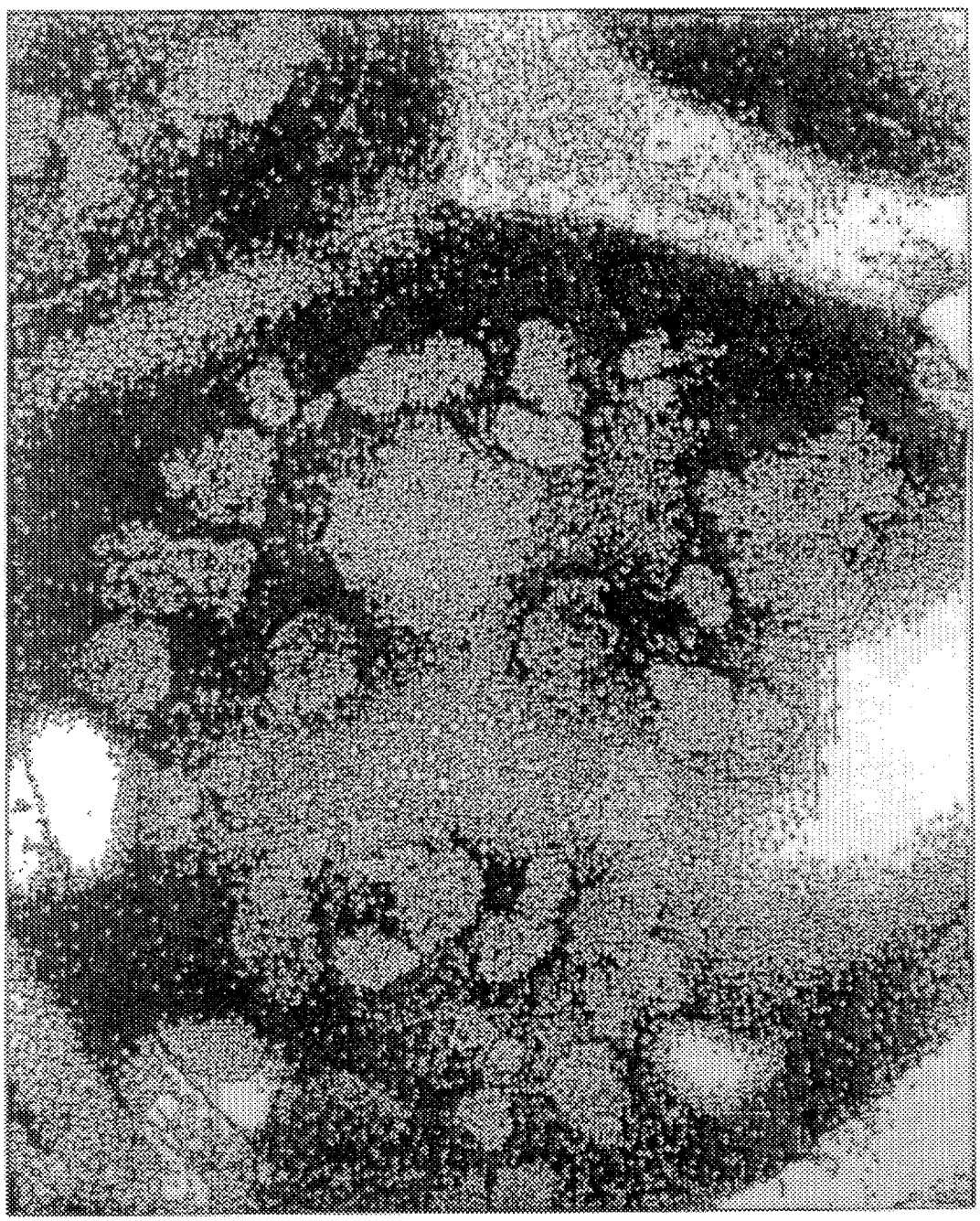

United States Patent [19]

Yoshimura et al.

[11] Patent Number: 5,670,624
[45] Date of Patent: Sep. 23, 1997

[54] TWO-DIMENSIONAL AGGREGATION AND FIXATION OF PROTEIN BY INJECTION INTO A SUBSTRATE SOLUTION HAVING HIGHER SURFACE TENSION AND SPECIFIC GRAVITY

[75] Inventors: Hideyuki Yoshimura, Ibaraki; Kuniaki Nagayama, Tokyo, both of Japan

[73] Assignee: Research Development Corporation of Japan, Saitama, Japan

[21] Appl. No.: 531,272

[22] Filed: Sep. 20, 1995

Related U.S. Application Data

[63] Continuation-in-part of Ser. No. 321,232, Oct. 11, 1994, abandoned.

[30] Foreign Application Priority Data

Oct. 12, 1993 [JP] Japan ............................ 5-253880

[51] Int. Cl.$^6$ .................. C07K 3/00; C12Q 1/00; C12N 11/00; C12N 11/02
[52] U.S. Cl. ................ 530/350; 435/4; 435/174; 435/177; 435/817; 530/810; 530/812
[58] Field of Search ........................ 435/174, 177, 435/817, 4; 530/412, 427, 350, 810, 812

[56] References Cited

U.S. PATENT DOCUMENTS

| | | | |
|---|---|---|---|
| 4,675,071 | 6/1987 | Matsumoto et al. | 156/621 |
| 5,102,798 | 4/1992 | Guiseppi-Elie | 435/177 |

*Primary Examiner*—David M. Naff
*Attorney, Agent, or Firm*—Wenderoth, Lind & Ponack

[57] ABSTRACT

Protein is two-dimensionally aggregated and fixed to produce a functional thin film. A denatured film of a first protein is formed on the surface of a substrate solution such as an aqueous sugar or salt solution. A solution of a second protein which may be the same as or different from the first protein is then injected below the surface of the substrate solution at a distance sufficient not to disturb the surface. The substrate solution has a higher surface tension and specific gravity than the second protein solution causing the second protein to float between the denatured protein film and the substrate solution surface to form the two-dimensionally aggregated and fixed protein. The denatured film of first protein may be formed by injection of a solution of the first protein below the surface of the substrate solution. The aggregated and fixed protein can be heated and then transferred onto a solid surface such as in the formation of a biosensor. A three-dimensional multilayer laminate of the two-dimensional aggregate may also be formed. In an alternative embodiment, a lipid monolayer is formed on the surface of the substrate solution, a protein solution is injected below the surface of the substrate solution and the protein floats between the substrate solution surface and the lipid monolayer to form the two-dimensionally aggregated and fixed protein.

12 Claims, 2 Drawing Sheets

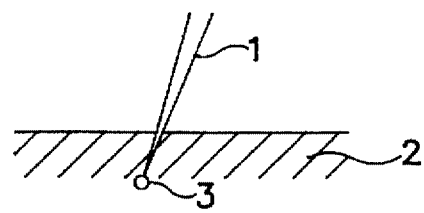
FIG. IA
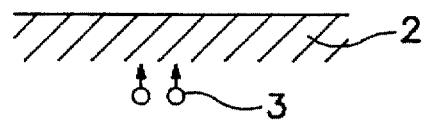
FIG. IB
FIG. IC
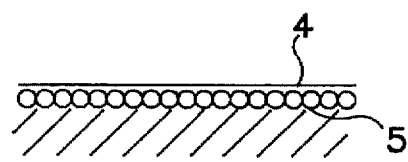
FIG. ID
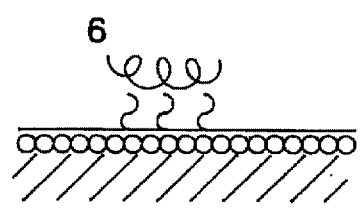
FIG. IE
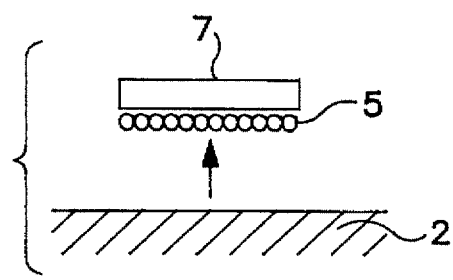
FIG. IF

TWO-DIMENSIONAL AGGREGATION AND FIXATION OF PROTEIN BY INJECTION INTO A SUBSTRATE SOLUTION HAVING HIGHER SURFACE TENSION AND SPECIFIC GRAVITY

CROSS REFERENCE TO RELATED APPLICATION

This is a continuation-in-part of U.S. Ser. No. 08/321,232 filed Oct. 11, 1994, now abandoned.

FIELD OF THE INVENTION

The present invention relates to a method of two-dimensional aggregation and fixation of proteins. More specifically, the present invention relates to a method of forming a high-quality proteinaceous two-dimensionally fixed aggregate excellent in uniformity, which is useful as a functional thin film or a three-dimensionally integrated functional film.

BACKGROUND OF THE INVENTION

It is believed that two-dimensional or three-dimensional structurization of protein is indispensable for next-generation substrate technologies such as molecular element, biosensor and biologically compatible materials. Positive efforts have therefore been made to find a method of structurizing protein at a higher accuracy.

Conventional technologies have several shortcomings, however.

The following representative methods of forming a two-dimensional aggregate of protein are known:

(a) a method of forming a two-dimensional crystalline aggregate by forming a lipid monolayer on the surface of a protein solution and using linkage with protein and fluidity; and (b) a method of developing a protein solution on the surface of a flat liquid metal such as mercury or mica or a solid and forming a crystalline aggregate during the drying process thereof.

It is also known, in these methods, that the protein solution is developed by using a substrate solution having a greater specific gravity and a greater surface tension than the protein solution, and dripping the protein solution onto the surface thereof.

In these conventional methods, however, the ratio of success has been very low because of the difficulty in selecting a proper lipid, non-uniformity increased by disturbance during dripping of the protein solution, and the difficulty in forming a two-dimensional aggregate of uniform protein particles. When using mercury, the process has inevitably been complicated as a result of troublesome handling, and the requirement for large, expensive equipment.

The conventional methods have another problem in that it is difficult to three-dimensionally laminate a two-dimensional aggregate into a multi-layer structure and a serious obstacle in building a three-dimensional protein structure has not as yet been solved. More specifically, protein may be denatured during the drying process in the conventional methods.

SUMMARY OF THE INVENTION

The present invention has therefore an object to provide a novel method for two-dimensional aggregation and fixation of protein particles, which solves the shortcomings of the conventional methods as described above, permits formation of a uniform and high-quality two-dimensional aggregate, easy three-dimensional lamination, and is applicable with simple equipment and easy operations.

As a means to solve the above-mentioned problems, the present invention provides a method of two-dimensional aggregation and fixation of protein, which comprises the steps of pouring a protein solution into a substrate solution having a higher surface tension and higher specific gravity than those of the protein solution, causing the protein solution to float and develop on the surface of the substrate solution to produce a denatured protein film on the surface, and causing said film to adsorb protein having been poured into the substrate solution and floated.

In the method of the present invention, conceivable embodiments include fixing a two-dimensional aggregate of protein particles into multiple layers by adjusting the concentration and amount of poured protein solution, heating the two-dimensionally aggregated and fixed protein aggregate to transcribe the same onto the solid substrate, and forming a protein denatured film using one kind of protein and two-dimensionally aggregating and fixing onto this denatured film another kind of protein.

Even when using a conventional lipid monolayer, the present invention provides a method of two-dimensional aggregation and fixation of protein, which comprises the steps of developing a lipid on the surface of a substrate solution having a higher surface tension and a higher specific gravity than those of a protein solution to produce a monolayer, pouring the protein solution into the substrate solution, causing the protein solution to float from the substrate solution to develop between the substrate solution and the lipid monolayer, and causing the lipid monolayer to adsorb protein to accomplish two-dimensional aggregation and fixation.

BRIEF DESCRIPTION OF THE DRAWINGS

FIGS. 1A–1F show a process diagram illustrating the method of the present invention.

FIG. 2 shows an electron micrograph showing two-dimensional aggregation and fixation of ferritin as an example.

DETAILED DESCRIPTION OF THE INVENTION

In the present invention, essentially unlike the conventional methods of dripping and developing a protein solution onto the surface, the protein solution is poured onto a substrate solution having a larger surface tension and a larger specific gravity than those of the protein solution, and then caused to float from this substrate solution for development. Disturbance of solution during development is inhibited, and uniformity is thus remarkably improved.

When forming a protein denatured film, furthermore, it is not necessary to form a lipid monolayer as the two-dimensional aggregate substrate, and according to the method of the present invention, it is easier to accomplish three-dimensional lamination. As a drying step is not required, even a protein not resistant to drying can be used, resulting in simple equipment and operations.

There is no particular limitation on the kind of protein; any protein originating from natural animals or vegetables, or available from synthesis may be used. While an aqueous solution is usually used, a non-aqueous solution is well applicable.

As a substrate solution having a higher surface tension and a higher specific gravity than the protein solution, there is no particular limitation on the kind thereof; a solution of sugar or an inorganic or organic salt may appropriately be adopted.

This is also the case using a lipid.

As described herein, a transmission electron microscope (TEM) investigation of protein films is obtained with a new, simple spreading technique that involves injection of the protein solution into the subphase (followed by smooth rising) rather than dropping the protein solution on the subphase (which disrupts the surface). This technique takes advantage of the buoyant force and the surface tension of protein solutions, which are important factors when the solutions and the subphase have different densities and surface tensions. The proteins form a thin, smooth monolayer of unfolded protein at the air-water interface. Two-dimensional protein arrays are obtained when enough intact protein is available to adsorb to this film. To promote the growth of the array in two dimensions, but not in three dimensions, a thin protein solution sandwiched between the smooth unfolded protein film and the dense aqueous subphase is considered to be crucial.

Now, the method of the present invention is described further in detail by way of examples.

EXAMPLES

Materials. Horse spleen holoferritin (with iron core) was purchased from Boehringer Mannheim and was used without further purification. Recombinant apoferritin (without iron core), for which the DNA sequence was cloned from horse liver was expressed in *E. coli* [Takeda, S. et al., *Biochim.Biophys.Acta*, 1174: 218 (1993)] and purified as described elsewhere [Banyard, S. et al., *Nature*, 271: 282 (1978)]. Recombinant *Thermoplasma acidophilum* proteasomes were isolated as described elsewhere [Puhler, G., et al., *EMBO J.*, 11: 1607 (1992)]. The chemical reagents (glucose (Merck), glycerol (Merck), dimethyl sulfoxide (Sigma), poly(ethylene glycol) 6000 (Fluka), MOPS (Merck), and MES (Dojindo)) were of the highest obtainable purity. The water was used distilled twice or purified by use of a Millipore filter apparatus.

Trough and Surface Tension Measurements. A homemade circular Teflon trough (15 mm diameter, 177 mm$^2$ surface area) was filled with an aqueous subphase (0.5 mL). The protein solutions (0.8–5 μL) were injected into the subphase with a Hamilton syringe (No. 701) using the method described below. The surface tension was measured at room temperature using a Wilhelmy plate (2×15 mm$^2$ filter paper) with a tension balance (Riegler & Kirstein, Wiesbaden). The accuracy was ±0.1 mN/m.

Electron Microscopy. The TEM grids were covered with either a continuous or a holey carbon film. The holey carbon grids were prepared according to the method described by Reichlet et al., *Micron*, 8:29 (1977). The film at the air-water interface was transferred by touching the grid horizontally (face to face) to the surface. Electron micrographs were taken under low electron dose conditions using either a Philips CM10 or JEOL JEM1200EX-II electron microscope (the total electron dose was less than 2000 e$^-$/nm$^2$). Negatives were digitized by use of a CCD camera system (Eikonix CCD camera 1412) or a microdensitometer (Perkin-Elmer Model 1010M). For image processing, the SEMPER and EMIDO (developed by ERATO) software systems were used.

With reference to FIGS. 1A–1F, the method of the present invention is as follows:

FIG. 1A. A solution (substrate solution) having a higher surface tension than water, which contains dissolved glucose and salts (NaCl, KCl or the like), is prepared, and a protein solution is poured into the substrate solution with an injector. At this point, specific gravity of the substrate solution is adjusted by glucose, salts, or heavy water (D$_2$O) so as to be larger than the protein solution.

FIG. 1B. Injected protein floats up to the surface by the difference in specific gravity.

FIG. 1C. When reaching the surface, the protein solution develops under the effect of the difference in surface tension with the substrate solution, and immediately, a denatured film of that protein is formed on the surface.

FIG. 1D. After a while, non-denatured protein is adsorbed by the denatured film, forming a two-dimensional crystalline aggregate, and is fixed. By adjusting the concentration and the amount of poured protein solution, it is possible to form a thin three-dimensional crystalline multi-layer structure.

In addition, as required,

FIG. 1E. A heat treatment (heating to 30° to 40° C., and then cooling slowly) is applied.

And then,

FIG. 1F. Transcription is performed onto a solid substrate: The protein two-dimensional aggregate is transcribed (transferred) onto a solid substrate such as a carbon film, quartz, or silicon, by physical adsorption, or in some cases, by chemical combination.

Spreading Method. The spreading of the protein solutions on water surfaces is usually done by dropping the solution onto the surface. With this method, the water surface is disturbed by surface vibration, resulting in poor reproducibility. To obtain better spreading, we injected the protein solution directly into the subphase solution. With the proper density and surface tension, the protein solution rises to the surface and spreads without any disturbance at the surface. This process was easily visible when using a holoferritin solution, which has a red color due to the iron core.

Aqueous Subphases. For testing the parameters that affect the spreading, modified aqueous subphases containing glucose (2,4,10, and 20%(w/v)), NaCl (0.5M), dimethyl sulfoxide (100%), poly(ethylene glycerol) (10%(w/v)), and glycerol (10% (v/v)) solutions were used. The densities and the surface tensions of these solutions are summarized in Table 1 hereinbelow.

TABLE 1

| | conc | temp (°C.) | surface tension γ(mN/m) | γH$_2$O-γ (mN/m) | density (g/cm$^3$) | spreading[a] |
|---|---|---|---|---|---|---|
| Water[b] | 100% | 18 | 73.05 | 0 | 0.99850 | |
| | 100% | 20 | 72.75 | 0 | .9982 | |
| glucose[c] | 2% (w/v) | ~20 | 75.6 | −2.8 | 1.02 | + |
| NaCl[b] | 0.5M | 20 | 73.8 | −1.0 | 1.02 | + |
| DMSO[c] | 100% | ~20 | 52.0 | +20.8 | 1.093[d] | + |
| PEG6000[c] | 10% (w/v) | ~20 | 66.0 | +6.8 | 1.1 | − |
| glycerol[b] | 10% (v/v) | 18 | 72.9 | +0.2 | 1.03 | − |

[a]For spreading, "+" indicates complete spreading and "−" indicates that the spread protein solution remained as a disk;
[b]CRC Handbook of Chemistry and Physics, 72th ed.; CRC Press; Boca Raton, FL 1991;
[c]Measurement at room temperature;
[d]Sigma catalog.

For optimum 2D array formation experiments, the aqueous subphase contained 2% glucose, 0.15M NaCl, 10 mM CdSO$_4$, and 10 mM MOPS (or MES) (pH 5.7).

The above-mentioned steps were performed using an aqueous solution of glucose and NaCl as the substrate solution using an aqueous solution of equine spleen ferritin, and a two-dimensional aggregate of protein ferritin was transcribed onto a carbon substrate. By controlling the ferritin concentration, a two-layer structure, and then structures with more than two layers, could be formed.

FIG. 2 is an electron micrograph showing an example of two-dimensional aggregation and fixation of the equine spleen ferritin. A monolayer two-dimensional crystalline aggregate is observed at the center, and a multi-layer two-dimensional aggregate, is observed locally at the position indicated by the arrow.

In this case, a denatured film may be formed, not with protein of the same kind, but with protein of a different kind. More specifically, the following steps may be followed:

1) Development of protein for forming a denatured film: Because protein is easily denatured, it is necessary to select a kind suitable for forming a uniform denatured film.

2) Development of protein becoming crystalline:

Alternatively, a lipid monolayer may be used. In this case, the following steps are followed:

1) Forming a lipid monolayer: A monolayer is formed by developing a lipid on a liquid having a larger specific gravity than a protein solution such as a glucose solution. The conventional crystallization method comprises directly forming a lipid monolayer on a protein solution. The protein may be denatured by an organic solvent dissolving the lipid in the conventional method.

2) Improving, as required, the quality of monolayer through application of compression and a heat treatment.

3) Developing protein from below the lipid monolayer (in the substrate solution such as a glucose solution). Protein floats up and forms a thin layer between the lipid monolayer and the substrate solution. This process requires a smaller amount of protein in total than in the conventional method.

Results and Discussion.

Aqueous Subphases. Different aqueous subphases including glucose, NaCl, dimethyl sulfoxide (DMSO), poly (ethylene glycol)(PEG 6000), and glycerol were tested to observe their efficiency in promoting spreading. The spreading of holoferritin solutions (5 mg/mL, 0.8 µL) was monitored with a CCD camera or observed by eye. Complete concentric spreading was obtained with glucose- and NaCl-containing subphases. On a DMSO subphase (100% DMSO), the holoferritin solution spread in a spokelike manner rather than concentrically. For subphases containing PEG and glycerol, the holoferritin solution rose to the surface and formed a circular disk that spread only slowly. On the glucose-containing subphase, the ferritin solution spread within 1 second. In contrast, on the glycerol-containing subphase the solution remained as a circular disk (6 mm diameter) for up to 30 seconds after it rose to the surface. A higher surface tension than water (Table 1) is considered to be important for fast spreading. Subphases with smaller surface tensions, such as glycerol and PEG, yielded incomplete spreading (Table 1). Although DMSO has a smaller surface tension than water, the holoferritin solution spread well though not concentrically. Thus, the spreading mechanism may involve other physicochemical properties instead of or in addition to the surface tension.

The film at the air-water interface was transferred to TEM grids covered with a carbon support film. When the subphase was DMSO or a concentrated glucose solution (higher than 10%), the transferred film had to be rinsed with water to produce clear negative stain images. Small assemblies of holoferritin arrays with hexagonal lattices were observed when the subphase was glucose and NaCl. A 2% glucose solution was used as the aqueous subphase in the following experiments.

Salt Conditions in the Subphase. It is known that the ions in protein solutions have an influence on protein-protein interactions. For successful crystallization of protein molecules, the salt conditions must therefore be optimized [Jap, B., et al., *Ultramicroscopy*, 46:45 (1992)]. To investigate the effect of salt ions on the ordering of holoferritin, various salts were used, and the resulting arrays were examined by TEM by transferring them to a carbon film. Electron micrographs with similar focus settings were digitized and their Fourier transforms calculated. The radial distribution functions of the power spectrums were obtained by averaging the power spectrum rotationally. The position and the half-width of the peak of the radial distribution functions were measured as a value of the packing state. In addition to the 2% aqueous glucose solution, NaCl(0.15M) was always included in the aqueous subphase to improve the reproducibility and uniformity of the film. The salts studied included $CdSO_4$, $CdCl_2$, $MgSO_4$, $MgCl_2$, $ZnCl_2$, and $MnCl_2$.

The line width is a criterion of the quality of the arrays; well-ordered arrays give sharper line widths and poorly ordered arrays give broader ones. The position of the peak is related to the averaged distance between molecules. The position of the peak usually correlates with the line width because closer molecular contacts tend to improve the quality of the lattice. The narrowest line width was observed with 10 mM $CdSO_4$. Therefore, the aqueous subphase with 2% glucose, 0.15M NaCl, and 10 mM $CdSO_4$ was selected for further crystallization experiments. In the initial experiments unbuffered solutions were used (pH about 6.0±0.5). The later experiments included 10 mM MOPS or MES to adjust the pH of the solution to 5.7.

Unfolding of Protein at the Air-Water Interface. Holoferritin solution (1 mg/mL, 1 µL) was spread on the subphase (2% glucose, 0.15M NaCl, 10 mM $CdSO_4$, and 10 mM MOPS (pH 5.7)), and the film formed at the air-water interface was transferred to a holey carbon film 5 minutes after spreading. Due to the iron core of holoferritin, it can easily be seen by TEM without staining. The holoferritin film covered most of the holes of the carbon film, though it was highly susceptible to damage by electron irradiation. To avoid this, the protein film was reinforced by a carbon coating [Jap, B., et al. Ibid.]. The film was rinsed with water from the other side to remove excess glucose. The presence of apparently isolated ferritin molecules across the hole confirms that these are supported by a thin amorphous film. This film is considered to be unfolded protein because no film could be detected for subphases that had not been injected with protein solution.

Growth of Two-Dimensional Protein Arrays under the Unfolded Protein Films. To investigate the time course of formation of the unfolded protein film, recombinant apoferritin (1 mg/mL, 1 µL) was spread on the same subphase as described above, and samples were taken after different time periods. The films were transferred to holey carbon films and negatively stained with 2% uranyl acetate after carbon reinforcement. One minute after the protein was spread, the holes of the carbon film were already observed to be covered with a smooth unfolded protein film. A few intact apoferritin molecules that were adsorbed onto this film were also observed. Three minutes after the protein was spread, the number of adsorbed apoferritin molecules increased, and small hexagonal arrays of apoferritin were observed. Apoferritin formed large domains of hexagonal arrays 10 minutes after the protein was spread. These observations suggest that the unfolding of protein molecules took place first and subsequently intact protein molecules adsorbed on the film.

The 2D arrays were also observed after transfer to continuous carbon support films. Compared with the holey carbon films, however, the frequency with which ordered arrays were successfully observed was much reduced. The unfolded protein films may have tended to dissociate from the carbon support film during the staining process. The carbon coating used to reinforce the unfolded protein films that were transferred to the holey carbon films would fix the film itself as well as the molecules adsorbed on the film.

When the total amount of protein spread on the surface was reduced to 0.5 μg (0.5 mg/mL, 1 μL) a film of unfolded protein with a small number of intact spherical molecules adsorbed onto it was observed. From this it is concluded that the total amount of protein required to cover the surface of the trough (177 mm$^2$) in form of an unfolded protein film was about 0.5 μg.

Crystallinity of 2D Arrays. To examine the crystallinity of two-dimensional arrays of apoferritin, correlation averaging of the TEM images [Saxton, W. O., et al. *J. Micros.*, 127:127 (1982); Frank, J. *Optik*, 63:67 (1982)] followed by displacement field analysis (DFA) [Durr, R. *Ultramicroscopy*, 38:135 (1991); Saxton, W. O., et al., *Ultramicroscopy*, 46:287 (1992)] were accomplished. The cross-correlation function between a small reference image extracted from the window-filtered image of the array and the original image of the array was calculated to determine the displacements of unit cells from the ideal lattice sites. More than 4500 correlation peaks (unit cells sites) with little displacement were found in the array, and the averaged image after compensation for the displacement of unit cells (correlation averaging) was calculated. As reported elsewhere [Yoshimura et al., *Ultramicroscopy*, 32:265 (1990)], the averaged image showed threefold symmetry, and the molecules are considered to be oriented with their threefold axes perpendicular to the crystal plane. Because the lattice displacements also exhibit local distortions of unit cells, the distortion (deformation and rotation) of the unit cells in the array was analyzed by DFA. The histograms of the deformation (magnification and elongation) and the rotation that were obtained showed a Gaussian distribution, and the calculated standard deviations ($\sigma$) of magnification, elongation, and rotation were 0.60%, 0.42% (against the first principal axes), and 0.30°, respectively. These small standard deviations reveal that the array is a crystal with only slight distortions.

Unfolded Protein Film at the Surface of Bulk Protein Solutions. Ordered 2D arrays (crystals) of apoferritin were obtained by spreading a protein solution on the surface of an aqueous subphase. The growth of 2D arrays may, however, also be done at the surface of bulk protein solutions without the need for the instant injection and spreading procedure. To examine this alternate method, protein films were transferred from the surface of bulk apoferritin solutions that had protein concentrations ranging from 0.003 to 0.9 mg/mL and the same type of solution conditions as the subphase (2% glucose, 0.15M NaCl, and 10 mM MES (pH 5.7) used for spreading experiments. In the presence of 10 mM $CdSO_4$, the apoferritin solutions became turbid ($CdSO_4$ had previously been used in 3D crystallization experiments for protein precipitation [Banyard, S. et al., Ibid.]. Unordered aggregates as well as thick 3D crystals were adsorbed onto the unfolded protein film, but no 2D arrays were found in this protein concentration range. In the absence of $CdSO_4$ only random adsorption of apoferritin molecules to the unfolded protein film was observed.

Surface Pressure of Spread Apoferritin and the Bulk Apoferritin Solution. The surface pressure of apoferritin (1 mg/mL, 1 μL) spread on the aqueous subphase increased up to 2.8 mN/m and was found to read a stable value 20 minutes after the protein was spread. No detectable surface pressure was observed when the total amount of spread protein was less than 0.5 μg. Also, no surface pressure was detected for the bulk apoferritin solution under the same solution conditions as those used in the spreading experiments. In the absence of $CdSO_4$, the surface pressure increased gradually.

Application of this Spreading Technique to Other Proteins. We applied this technique to proteasome (a multicatalytic proteinase) using the same subphase conditions as used for ferritin (2% glucose, 0.15M NaCl, 10 mM $CdSO_4$, with 10 mM MOPS (pH 5.7)). A 1 μL protein solution with a concentration of 0.15 mg/mL was injected five times to supply enough protein molecules to form both the unfolded protein film and adsorbed intact molecules below that. The proteasomes were found to also form an unfolded protein film to which small hexagonal arrays comprised of 40–50 adsorbed molecules were observed.

Unfolded Protein Film at the Air-Water Interface. According to Bull [Bull, H. B., et al., *J.Biol.Chem.*, 185:27 (1950)], the smallest occupied area of unfolded protein is 0.78 m$^2$/mg of protein, independent of the species of protein. Using this value for our system, 0.23 μg of protein is required to completely cover the surface of the 177 mm$^2$ trough. When 1 μg of apoferritin is spread, 23% of the total protein should cover the water-air interface as unfolded protein film, and 77% of the total protein should remain intact. Because the smallest occupied area of an intact spherical ferritin molecule is 133 nm$^2$ (0.18 m$^2$/mg protein), the rest of the spread protein (0.77 μg) can cover 79% of the area under the unfolded protein film. This rough estimation well explains the observed density of adsorbed apoferritin molecules on the film. Because almost all of the protein is incorporated in either the unfolded protein film or the adsorbed molecules, the amount of protein that diffuses into the subphase appears to be negligible.

Surface Pressure of the Unfolded Protein Films. The surface pressure due to the unfolded film was estimated to be very small (less than the instrumental limit of 0.2 mN/m) because no significant increase in surface pressure was detected when the amount of the spread protein was increased up to 0.5 μg (the point at which unfolded protein film formation is complete).

Adsorption of Apoferritin Molecules onto the Unfolded Protein Film. The gradual increase and then leveling off of the surface pressure after the protein was spread was observed. This effect can be explained as being due to the adsorption of intact apoferritin molecules to the unfolded protein film. The gradual increase in the surface pressure of the bulk protein solution occurred because protein molecules can be supplied from the bulk phase without limitation. The leveling off of the surface pressure is considered to be due to the limited supply of protein molecules from the thin solution layer on the aqueous subphase. In the presence of $CdSO_4$, the surface pressure of the bulk apoferritin solution was below the limits of measurement. Under these conditions, apoferritin molecules aggregated and the solution became turbid. Adsorption of isolated solid aggregates to the unfolded protein film does not appear to contribute to the surface pressure because of lack of interaction between the aggregates.

Furuno et al. [Furuno, T., et al. *Thin solid Films*, 180:23 (1989)] reported the adsorption of ferritin to a positively charged polypeptide (poly(1-benzyl-L-histidine)) layer at the air-water interface. Because the isoelectric point of ferritin is about pH 4.8 [Urushizaki, I., et al., *Biochim.Biophys.Acta*, 243:187 (1971)], resulting in ferritin molecules having a negative charge at neutral pH, ferritin is able to bind to a positively charged layer. Though the unfolded ferritin film is considered to have the same charge as the intact ferritin molecule (negative charge at pH 5.7), the unfolded protein has both positively and negatively charged amino acids distributed throughout the structure. In these experiments, intact ferritin likely binds to the positively charged sites of the unfolded polypeptide chains.

Growth of 2D Arrays. We observed 2D protein arrays only when protein solutions were spread underneath the air-water interface. The formation of a thin protein solution layer on the aqueous subphase appears to confine the growth of the array in two dimensions. According to Bull [Bull, H. B., *Adv. Protein Chem.*, 3:95 (1947)], the thickness of the unfolded protein film is about 1 nm, which corresponds roughly to the thickness of a polypeptide chain. This thin and flat film (on a nanometer scale) appears to provide an ideal substrate for 2D crystallization. We obtained small hexagonal arrays of the proteasomes on the unfolded protein film. Because it is generally expected that proteins will unfold at the air-water interface and form monolayers, this technique should work for many other water-soluble proteins.

According to the method of the present invention, as described above in detail, the following advantages are achieved:

(1) Since the protein solution is poured into a substrate solution having a larger specific gravity and a larger surface tension than those of the protein solution, and protein floats up to develop on the surface, disturbance of solution upon development and non-uniformity are alleviated.

(2) It is not necessary to form a lipid monolayer as a two-dimensional crystallization substrate, because a surface denatured film is utilized.

(3) A thin three-dimensional crystalline aggregate can be formed by increasing the amount of protein to be developed.

(4) Only simple and low-cost equipment is required.

(5) Because of the absence of a drying process, the present invention is applicable to a protein not resistant to drying.

Although the invention has been described in detail by way of illustration and example, it should be apparent that certain obvious modifications can be practiced within the scope of the appended claims.

What is claimed is:

1. A method of two-dimensionally aggregating and fixing a protein comprising:

forming a denatured film of a first protein on the surface of a substrate solution selected from the group consisting of an aqueous sugar solution, an aqueous salt solution and a mixture thereof;

injecting a solution containing a second protein by means of an injector syringe sufficiently below the surface of the substrate solution so as to avoid disturbance of the surface thereof, which substrate solution has a higher surface tension and a higher specific gravity than said second protein solution;

causing at least a portion of said second protein to float on the substrate solution between the substrate solution and said denatured protein film; and causing said denatured protein film to adsorb said second protein and form said two-dimensionally aggregated and fixed protein on said denatured protein film.

2. The method as in claim 1, wherein said first protein is identical to said second protein and said denatured film is formed by injecting a solution containing said first protein into the substrate solution and causing at least a portion of said first protein to float on the substrate solution.

3. The method as in claim 1, wherein said second protein is formed as multiple layers on the denatured protein film.

4. The method as in claim 1, wherein said first protein and said second protein are different.

5. The method as in claim 1, wherein the sugar solution is a glucose solution and the salt solution is a NaCl solution.

6. The method as in claim 1, wherein the two-dimensionally aggregated and fixed protein is heated and is then transferred onto a solid substrate.

7. The method as in claim 6, wherein said solid substrate is a carbon film.

8. A method of two-dimensionally aggregating and fixing a protein comprising:

forming a lipid monolayer on the surface of a substrate solution selected from the group consisting of an aqueous sugar solution, an aqueous salt solution and a mixture thereof;

injecting a solution containing said protein by means of an injector syringe sufficiently below the surface of the substrate solution so as to avoid disturbance of the surface thereof, which substrate solution has a higher surface tension and a higher specific gravity than said protein solution;

causing at least a portion of the protein to float on the substrate solution between the substrate solution and the lipid monolayer; and causing the lipid monolayer to adsorb the protein and form said two-dimensionally aggregated and fixed protein on the lipid monolayer.

9. The method as in claim 8, wherein the protein is formed as multiple layers on the denatured protein film.

10. The method as in claim 8, wherein the sugar solution is a glucose solution and the salt solution is a NaCl solution.

11. The method as in claim 8, wherein the two-dimensionally aggregated and fixed protein is heated and is then transferred onto a solid substrate.

12. The method as in claim 11, wherein said solid substrate is a carbon film.

* * * * *